United States Patent [19]
Tomiyama et al.

[11] Patent Number: 4,735,955
[45] Date of Patent: Apr. 5, 1988

[54] 2-SUBSTITUTED CYCLOHEPTOIMIDAZOLE DERIVATIVES AND ANTI-ULCERATIVE AGENTS CONTAINING THE SAME

[75] Inventors: Tsuyoshi Tomiyama, Sakaki; Akira Tomiyama, Togura, both of Japan

[73] Assignee: Kotobuki Seiyaku Co., Ltd., Nagano, Japan

[21] Appl. No.: 827,274

[22] Filed: Feb. 6, 1986

[30] Foreign Application Priority Data

Feb. 6, 1985 [JP] Japan .................................. 60-19852

[51] Int. Cl.$^4$ ................. A61K 31/415; A61K 31/445; C07D 235/02; C07D 401/12
[52] U.S. Cl. ..................... 514/338; 514/363; 514/365; 514/374; 514/378; 514/394; 514/393; 546/278; 548/136; 548/181; 548/235; 548/247; 548/323; 548/327
[58] Field of Search ............... 546/278; 548/136, 181, 548/235, 247, 327, 323; 514/338, 363, 365, 374, 378, 394, 393

[56] References Cited

U.S. PATENT DOCUMENTS 3,320,272  5/1967  Sunagawa et al. .................. 548/323

FOREIGN PATENT DOCUMENTS 1080912  8/1967  United Kingdom ................ 548/323

Primary Examiner—Henry R. Jiles
Assistant Examiner—Kurt G. Briscoe
Attorney, Agent, or Firm—Emmanuel J. Lobato; Robert E. Burns

[57] ABSTRACT

Derivatives of 2-substituted-cycloheptoimidazole are disclosed, which are represented by the following formula:

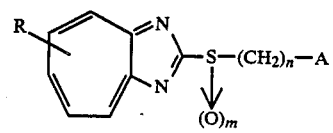

wherein R is a hydrogen atom, a lower-alkyl, acetyl, lower-alkylaminoalkyl or ethylenedioxyethyl group. A represents a phenyl, pyridyl, benzimidazolyl, imidazolyl, thiazolyl, thiadiazolyl, oxazolyl or isoxazolyl group; each of which optionally possesses one substituent or more and m is 0 or 1, and n is 1 or 2. These compounds are useful as anti-ulcerative agents.

7 Claims, No Drawings

2-SUBSTITUTED CYCLOHEPTOIMIDAZOLE DERIVATIVES AND ANTI-ULCERATIVE AGENTS CONTAINING THE SAME

BACKGROUND OF THE INVENTION

This invention relates to new 2-substituted cycloheptoimidazole derivatives and their acid addition salts, a method of their synthesis and their use as potent anti-ulceratives.

There have heretofore been used conventional antigastric ulceratives which may inhibit the secretion of gastric juice principally by their anti-cholinergic or anti-histaminic activities.

Under the present circumstances, it is desirable to have materials which are effective to inhibit the secretion of gastric juice by preventing $(H^+,K^+)$ATPase in the process of formation of HCl, when $Cl^-$ acts on $H^+$ secreted by said $(H^+,K^+)$ATPase in the gastric membrane.

SUMMARY OF THE INVENTION

The principal object of the present invention is the provision of compounds having $(H^+,K^+)$ATPase inhibitory activities.

Another object of the present invention is the provision of pharmaceutical compositions useful as anti-peptic ulcerative agents.

Still other objects of the present invention are the provision of 2-substituted-cycloheptoimidazole derivatives and a method for the manufacture thereof.

These and other objects of the invention will become apparent from the following description.

DETAILED DESCRIPTION OF THE INVENTION

The compounds of the present invention have the following general formula (1):

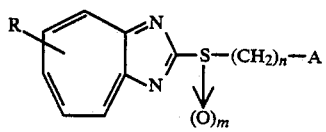

wherein R is hydrogen, lower alkyl, acetyl, lower alkylaminoalkyl or 1-ethylene dioxyethyl, m=0 or 1, n—1 or 2. A is a substituted or unsubstituted group such as phenyl, pyridyl, benzimidazolyl, imidazolyl, thiazolyl, pyrazolyl, thiadiazolyl, oxazolyl or isoxazolyl.

Substituted groups of A in general formula I include lower alkyl, such as methyl amino, mono- or di-loweralkylamino, such as methylaminomethyl, nitro, methoxy, chloro, phenyl, substitute phenyl, piperidinomethyl, piperidinocarbonyl, methylenedioxy, diethoxymethyl or guanidino group. and their pharmacologically acceptable acid-addition salts.

The compounds indicated by general formula I possess a potent anti-gastric ulcerative activity and they are regarded as therapeutically useful.

The compounds related to the general formula (I) are exemplified as follows:

(1) 2-(2-Pyridyl)methylthio-6-isopropyl-cycloheptoimidazole.
(2) 2-(2-Methylbenzimidazole-1-yl)ethylthio-cycloheptoimidazole.
(3) 2-(1-Benzimidazolyl)ethylthio-cycloheptoimidazole.
(4) 2-(2-Aminobenzimidazole-1-yl)ethylthio-cycloheptoimidazole.
(5) 2-(0-Piperidinocarbonylphenyl)methylthio-cycloheptoimidazole.
(6) 2-(2-Pyridyl)methylthio-cycloheptoimidazole.
(7) 2-(2,3-Methylenedioxyphenyl)methylthio-cycloheptoimidazole.
(8) 2-(2-Methylthio-1,3,4-thiadiazole-5-yl)methylthio-cycloheptoimidazole.
(9) 2-(3-Pyridyl)methylthio-cycloheptoimidazole.
(10) 2-(5-Pyrazolyl)methylthio-cycloheptoimidazole.
(11) 2-(2-Diethoxymethylpyridine-6-yl)-methyltio-cycloheptoimidazole.
(12) 2-(4-Pyridyl)methylthio-cycloheptoimidazole.
(13) 2-(4-imidazolyl)methylthio-cycloheptoimidazole.
(14) 2-(2-Aminothiazole-4-yl)methylthio-cycloheptoimidazole.
(15) 2-(2-Aminothiazole-4-yl)methylthio-6-isopropyl-cycloheptoimidazole.
(16) 2-(2-Methylaminomethylpyridine-6-yl)methylthio-cycloheptoimidazole.
(17) 2-(2-Piperidinomethylpyridine-6-yl)methylthio-cycloheptoimidazole.
(18) 2-(4-imidazolyl)methylthio-6-isopropyl-cycloheptoimidazole.
(19) 2-(2-Guanidinothiazole-4-yl)methylthio-cycloheptoimidazole.
(20) 2-(2-Guanidinothiazole-4-yl)methylthio-6-isopropyl-cycloheptoimidazole.
(21) 2-(4-imidazolyl)methylthio-6-(1-ethylenedioxyethyl)cycloheptoimidazole.
(22) 2-(2-Pyridyl)methylthio-6-(1-ethylenedioxyethyl)-cycloheptoimidazole.
(23) 2-(p-Nitrophenyl)methylthio-cycloheptoimidazole.
(24) 2-(2,3,4-Trimethoxyphenyl)methylthio-cycloheptoimidazole.
(25) 2-(o-Nitrophenyl)methylthio-cycloheptoimidazole.
(26) 2-(p-Methoxyphenyl)methylthio-cycloheptoimidazole.
(27) 2-(p-Tolyl)methylthio-cycloheptoimidazole.
(28) 2-(p-Chlorophenyl)methylthio-cycloheptoimidazole.
(29) 2-(p-Dimethylaminophenyl)methylthio-cycloheptoimidazole.
(30) 2-(m-Aminophenyl)methylthio-cycloheptoimidazole.
(31) 2-(Phenyl)methylthio-cycloheptoimidazole.
(32) 2-(2-Pyridyl)methylthio-5-acetyl-cycloheptoimidazole.
(33) 2-(2-imidazolyl)methylthio-5-acetyl-cycloheptoimidazole.
(34) 2-(5-Methylisoxazole-4-yl)methylthio-cycloheptoimidazole.
(35) 2-(3,5-Dimethylisoxazole-4-yl)methylthio-cycloheptoimidazole.
(36) 2-(3-Methylisoxazole-5-yl)methylthio-cycloheptoimidazole.
(37) 2-(2-Methyl-4-Phenyloxazole-5-yl)methylthio-cycloheptoimidazole.
(38) 2-[2-Methyl-4-(p-tolyl)-oxazole-5-yl]methylthio-cycloheptoimidazole.
(39) 2-[2-Methyl-4-(p-methoxyphenyl)-oxazole-5-yl]methylthio-cycloheptoimidazole.
(40) 2-[2-Methyl-4-(p-chlorophenyl)-oxazole-5-yl]methylthio-cycloheptoimidazole.
(41) 2-[3-Phenyl-5-methylisoxazole-4-yl]methylthio-cycloheptoimidazole

(42) 2-(2-Pyridyl)methylthio-5-(1-methylaminoethyl)-cycloheptoimidazole.
(43) 2-(4-Nitrophenyl)methylthio-cycloheptoimidazole-S-oxide.
(44) 2-(2,3,4-Trimethoxyphenyl)methylthio-cycloheptoimidazole-S-oxide.
(45) 2-(p-Tolyl)methylthio-cycloheptoimidazole-S-oxide.
(46) 2-(2-Methyl-4-phenyloxazol-5-yl)methylthio-cycloheptoimidazole.
(47) 2-(p-Methoxyphenyl)methylthio-cycloheptoimidazole-S-oxide.
(48) 2-Pyridylmethylthio-cycloheptoimidazole-S-oxide.
(49) 2-(p-Dimethylaminophenyl)methylthio-cycloheptoimidazole-S-oxide.
(50) 2-(3-Pyrazolyl)methylthio-cycloheptoimidazole-S-oxide.
(51) 2-(4-imidazolyl)methylthio-cycloheptoimidazole-S-oxide.
(52) 2-(3-Methylisoxazole-5-yl)methylthio-cycloheptoimidazole-S-oxide.
(53) 2(3,5-Dimethylisoxazole-4-yl)methylthio-cycloheptoimidazole-S-oxide.
(54) 2-(o-aminophenyl)methylthio-cycloheptoimidazol-S-oxide
(55) 2-(o-dimethylaminophenyl)methylthio-cycloheptoimidazol-S-oxide
(56) 2-(o-methylaminophenyl)methylthio-cycloheptoimidazole-S-oxide
(57) 2-(o-aminophenyl)methylthio-cycloheptoimidazol
(58) 2-(o-dimethylaminophenyl)methylthio-cycloheptoimidazol
(59) 2-(o-methylaminophenyl)methylthio-cycloheptoimidazol The above-mentioned compounds numbered from 1 to 59 will be referred to hereinafter, as compound 1, compound 2, ... compound 59 respectively.

The compound of general formula (I) can be obtained by reaction of the compound shown by the general formula (II) with a compound of the general formula (III).

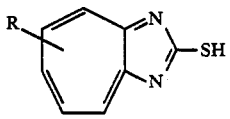

wherein R is the same as mentioned above

X—(CH$_2$)$_n$—A  (III)

wherein X is a halogen atom, n=1 or 2, and A is the same as mentioned above

The compounds shown by the general formula (II) can be prepared by reaction of the compound of general formula (IV) with thiourea according to the method of R. Shoji et al (Chemical Abstract 70, 77546K)

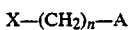

(IV)    (II)

In case R is acetyl the general formula (IV), in this reaction, the acetyl group is protected as the 1-ethylenedioxyethyl group, then reacted with thiourea following with X—(CH$_2$)$_n$ A and finally deprotected with dilute mineral acid, such as diluted hydrochloric acid, to obtain the desired compound.

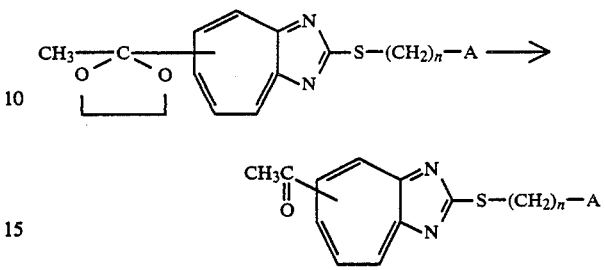

Furthermore, the acetyl group is converted to a lower alkylaminoalkyl group with R—NH$_2$ (R is lower alkyl) and NaBH$_4$.

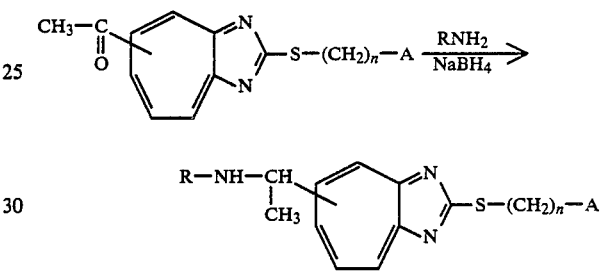

Most of the compounds shown in general formula (III) are obtained by a known method, but the compound of general formula (III) having the structure is obtained as follows (Compound 5),

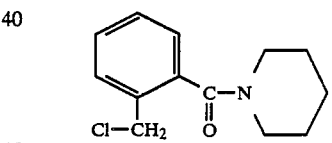

Phthalide is reacted with piperazine and then subjected to chlorination.

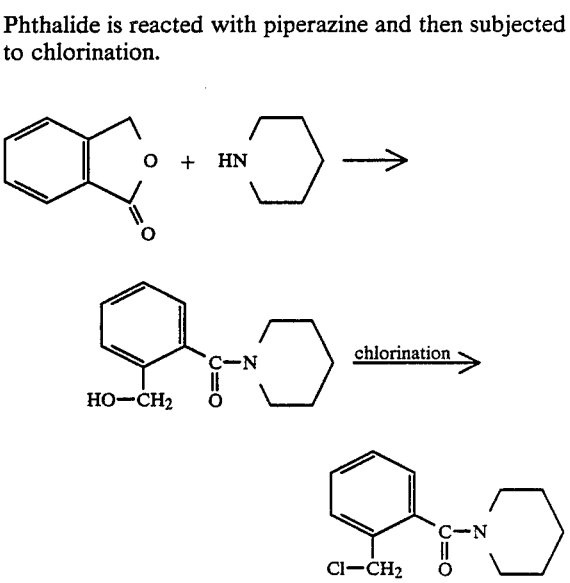

In case the compound in general formula (III) is compound 16 or compound 17, it is prepared by the following reaction.

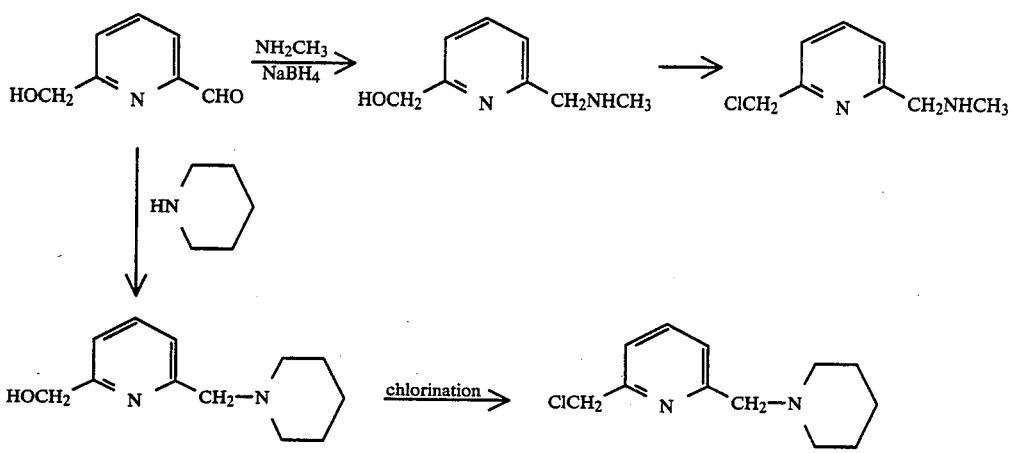

The compound of general formula (III) of the structure

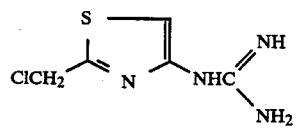

is prepared by the following reaction.

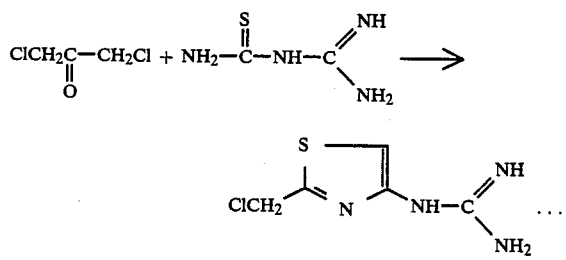

The reaction of the compound shown in formula (II) and formula (III) can be generally carried out in the presence of a base. A base is used in this reaction such as pyridine, triethylamine sodium hydroxide, potassium hydroxide, sodium carbonate potassium carbonate or sodium ethoxide.

As the solvent used in this reaction it is recommended to use a compound such as ethanol, acetone, tetrahydrofuran or water and the reaction proceeds at ambient or elevated temperature. The reactonn product can be purified in the usual manner such as recrystallization or column chromatography. The compound in general formula (I), wherein m=1, can be obtained by oxidizing the sulfide compound, which is prepared in the above mentioned manner.

As oxidizing reagents which can be used, common reagents are available such as peroxyacetic acid, m-chloroperoxybenzoic acid, 3,5-dinitroperoxybenzoic acid or hypohalogenide, for example.

It is recommended by carry out this oxidizing reaction at low temperature (−30°∼0°). As solvents which can be used, the following are available: benzene, toluene, dichloroethane or ethyl acetate.

The compounds of general formula (I) of this invention thus obtained show excellent anti-gastric juice secretion activity and are promising for therapeutic use.

The compounds of general formula (I) of this invention can be applied as anti-ulceratives in the form of their pharmaceutically acceptable acid-additions, for instance, hydrochloride, sulfate, citric acid or fumaric acid. For pharmaceutical purposes, the compounds of the present invention are administered orally, parenterally or rectally as active ingredients. One effective dosage, depending on age and symptom, is from 10 mg to 50 mg a day for adults. The following examples illustrate typical pharmaceutical dosage unit compositions comprising a compound of the present invention as an active ingredient.

Pharmaceutical Example 1

The following ingredients are used.

| | |
|---|---|
| Compound 45 | 50 mg |
| Lactose | 40 mg |
| Corn starch | 57 mg |
| Methylcellulose | 3 mg |
| Total | 150 mg |

Preparation

The ingredients are well mixed with each others and the resulting mixture is granulated in a conventional manner.

Pharmaceutical Example 2 tablets of following ingredients.

| | |
|---|---|
| Compound 51 | 30 mg |
| Lactose | 30 mg |
| Corn starch | 45 mg |
| Methylcellulose | 3 mg |
| Magnesium stearate | 2 mg |
| Total | 110 mg |

The following examples show pharmacological activity of the compounds of this invention and their preparation.

Pharmacological data 1

Gastric acid antisecretory activities

Inhibitory activities of gastric-acid secretion are determined by the method of Shay (Gastroenterology 26, 906). Rats are fasted for 24 hours and pylorus ligation is carried out under light anesthesia.

Drug is given intraduodenally just after the ligation. Four hours after ligation, the stomach of the rat is removed and the acidity of gastric juice is determined.

Results are shown in table 1

TABLE 1

| Test Compound | Dose (mg/kg) | Total Acid Inhibition (%) |
| --- | --- | --- |
| Compound 1 | 50 | 80.5 |
| Compound 3 | 50 | 22.4 |
| Compound 7 | 50 | 23.3 |
| Compound 8 | 50 | 20.6 |
| Compound 10 | 50 | 54.4 |
| Compound 12 | 50 | 66.8 |
| Compound 13 | 50 | 66.5 |
| Compound 15 | 50 | 21.0 |
| Compound 26 | 50 | 81.6 |
| Compound 28 | 50 | 39.1 |
| Compound 30 | 50 | 52.5 |
| Compound 31 | 50 | 78.9 |
| Compound 34 | 50 | 70.1 |
| Compound 44 | 50 | 89.8 |
| Compound 45 | 50 | 90.7 |
| Compound 47 | 50 | 90.7 |
| Compound 49 | 50 | 33.6 |
| Compound 51 | 50 | 63.6 |
| Compound 52 | 50 | 96.9 |
| Compound 53 | 50 | 95.7 |
| Compound 57 | 50 | 92.9 |

Pharmacological data 2

Cytoprotective Activities

Inhibitory activities of ethanol-induced ulcer are determined by the method of Robert (Gastroenterology 77, 433~443). Rats are fasted for 24 hours and are given 1 ml of absolute ethanol perorally. One hour after administration of ethanol, the stomach of the rat is removed. The length of each ulcer occurring in the grandulor stomach is determined and each ulcer in one rat is accounted as the ulcer-index. The test compounds are given perorally 30 minutes before absolute ethanol administration. The results are shown in table 2.

TABLE 2

| Test compound | Dose (mg/kg) | Inhibition (%) |
| --- | --- | --- |
| Compound 9 | 100 | 83.1 |
| Compound 13 | 100 | 88.1 |
| Compound 14 | 100 | 90.3 |
| Compound 15 | 100 | 90.0 |

Pharmacological data 3

Inhibition of $(H^+,K^+)$ATPase activities. Inhibition of $(H^+,K^+)$ ATPase activities is determined by the method of F. Fellenius et al., Nature 290, pp. 159~161, 1981. $(H^+,K^+)$ATPase is prepared from the pig gastric mucosa and the test compound is incubated with 2 mM of ATPase, 40 mM of tris-buffer (pH 7.4), 2 mM of $MgCl_2$ and 10 mM of KCl at 37° C. Inorganic phosphate occurring by stimulation of ATPase is determined. The results are shown in table 3.

TABLE 3

| Compound | Concentration (M) | % of Inhibition |
| --- | --- | --- |
| 37 | $3 \times 10^{-4}$ | 48 |
| 44 | $3 \times 10^{-4}$ | 25 |
| 47 | $3 \times 10^{-4}$ | 32 |
| 53 | $3 \times 10^{-4}$ | 45 |
| 57 | $3 \times 10^{-4}$ | 46 |

Reference Example 1

2-Mercapto-6-isopropyl-cycloheptoimidazole (1) 5-isopropyltropolone methyl ether.

A solution of diazomethane (prepared from 13.4 g of nitrosomethylurea) was added to a solution of 5-isopropyltropolone (16.4 g) and THF (100 ml) after the solution was stirred overnight, and the solution was evporated in vacuo. 18.2 g of the desired compound was obtained as pale yellow oil.

(2) 2-Mercapto-6-isopropyl-cycloheptoimidazole.

Sodium metal (1.15 g) was dissolved in ab. methanol (100 ml) and thiourea was added to this solution. To this solution 8.9 g of 5-isopropyltropolone was added. After allowing it to stand overnight, the solution was evaporated. The residue was diluted with 50 ml of water and warmed to about 70° C. After acidifying this solution with acetic acid, the resulting precipitate was collected. 5.3 g of the desired compound was obtained. m.p. 240° C. (decomp.) M.S. (m/e) 204 ($M^+$).

EXAMPLE 1

2-(2-pyridylmenthylthio)-6-isopropyl-cycloheptoimidazole. (Compound 1)

0.4 g of sodium hydroxide was dissolved in 1 ml of water and diluted with 10 ml of ethanol. To this solution 2.04 g of 2-mercapto-6-isopropyl-cycloheptoimidazole and 0.8 g of 2-chloromethylpyridine were added.

After standing overnight with stirring, the solvents were removed under reduced pressure. The residue was dissolved in ethyl acetate and washed with water. The ethyl acetate solution was extracted with the 5% hydrochloride solution and 5% hydrochloride layer was neutralized with 10% sodium hydroxide solution. The solid that was formed was isolated by filtration and recrystallized from ether;. 0.68 g of yellow crystal was obtained. m.p. 68°~69° C. M.S. (m/e) 295 ($M^+$) I.R. 1590, 1468, 1427, 1330 $cm^{-1}$.

EXAMPLE 2

Compound 2, . . . Compound 31 and compounds 57–59 can be obtained in the same manner as the method of Example 1. Chemical structures and melting points are shown in table 4.

EXAMPLE 3

2-(2-pyridyl)methylthio-5-acetyl-cycloheptoimidazole. (Compound 32)

0.5 g of compound 21 (prepared by the method of example 2) was added to a 10% HCl solution (5 ml). The mixture was heated on a steam bath for 2 hours and neutralized with 10% NaOH solution. The solution was extracted with chloroform. The chloroform extract was washed, dried ($Na_2SO_4$), then concentrated to dryness in vacuo. Purification of the residue by chromatography [$SiO_2$, $CHCl_3$-MeOH (100:1)] gave 0.15 g of the desired compound. m.p. 143°~144° C. M.S. (m/e) 295 ($M^+$). I.R. 1675, 1405, 1355, 1300 $cm^{-1}$.

EXAMPLE 4

2-(2-imidazolyl)methylthio-5-acetyl-cycloheptoimidazole. (Compound 33)

Compound 33 was obtained from compound 22 (prepared by the method of example 2) by the same procedure as outlined in example 3. m.p. 151°~153° C. M.S.

(m/e) 284 (M+) I.R. 3075, 2870, 1680, 1405, 1355, cm$^{-1}$.
TABLE 4
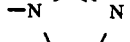
| Compound | R | n | A | m.p. (°C.) |
|---|---|---|---|---|
| 2 | H | 2 | 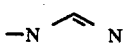 | 191~192° C. |
| 3 | H | 2 | 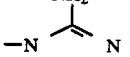 | 152~153° C. |
| 4 | H | 2 | 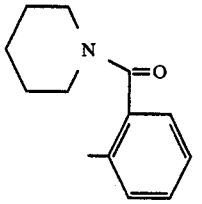 | 241~242° C. |
| 5 | H | 1 | 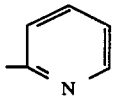 | 84~86° C. |
| 6 | H | 1 | 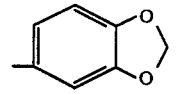 | 79~81° C. |
| 7 | H | 1 | 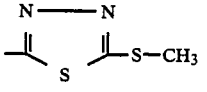 | 150~152° C. |
| 8 | H | 1 | 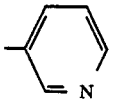 | 75~78° C. |
| 9 | H | 1 | 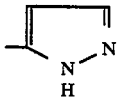 | 140~141° C. |
| 10 | H | 1 |  | 154~155° C. |

TABLE 4-continued

Structure: R—[benzimidazole]—S—(CH$_2$)$_n$—A

| Compound | R | n | A | m.p. (°C.) |
|---|---|---|---|---|
| 11 | H | 1 | 2-pyridyl-CH(OC$_2$H$_5$)$_2$ | Oil |
| 12 | H | 1 | 4-pyridyl | 115~117° C. |
| 13 | H | 1 | 1H-imidazol-4-yl | 83~85° C. |
| 14 | H | 1 | 2-amino-thiazol-4-yl | 163~164° C. |
| 15 | 6-isopropyl | 1 | 2-amino-thiazol-4-yl | 159~161° C. |
| 16 | H | 1 | 6-(CH$_2$NHCH$_3$)-pyridin-2-yl | 185~187° C. |
| 17 | H | 1 | 6-(CH$_2$-piperidin-1-yl)-pyridin-2-yl | Oil |
| 18 | 6-isopropyl | 1 | 1H-imidazol-4-yl | 132~134° C. |
| 19 | H | 1 | 2-(guanidino)-thiazol-4-yl | 205~206° C. |
| 20 | 6-isopropyl | 1 | 2-(guanidino)-thiazol-4-yl | 227° C. |
| 21 | 2,2-dimethyl-1,3-dioxolan-4-yl (6-position) | 1 | 1H-imidazol-4-yl | 110~113° C. |
| 22 | 2,2-dimethyl-1,3-dioxolan-4-yl (6-position) | 1 | 2-pyridyl | 86~88° C. |

TABLE 4-continued structure: R-[bicyclic imidazole]-S-(CH₂)ₙ-A

| Compound | R | n | A | m.p. (°C.) |
|---|---|---|---|---|
| 23 | H | 1 | 4-NO₂-C₆H₄- | 174~175° C. |
| 24 | H | 1 | 2,3,4-(CH₃O)₃-C₆H₂- | 99~100° C. |
| 25 | H | 1 | 2-NO₂-C₆H₄- | 135~136° C. |
| 26 | H | 1 | 4-OCH₃-C₆H₄- | 82~84° C. |
| 27 | H | 1 | 4-CH₃-C₆H₄- | 104~106° C. |
| 28 | H | 1 | 4-Cl-C₆H₄- | 112~113° C. |
| 29 | H | 1 | 4-N(CH₃)₂-C₆H₄- | 134~136° C. |
| 30 | H | 1 | 3-NH₂-C₆H₄- | 130~132° C. |
| 31 | H | 1 | C₆H₅- | 94~95° C. |
| 57 | H | 1 | 2-NH₂-C₆H₄- | 243~245° C. |

TABLE 4-continued

Structure: R-[cycloheptoimidazole]-S-(CH₂)ₙ-A

| Compound | R | n | A | m.p. (°C.) |
|----------|---|---|---|------------|
| 58 | H | 1 | 2-(N(CH₃)₂)-phenyl | 80~81° C. |
| 59 | H | 1 | 2-(NHCH₃)-phenyl | 124° C. |

EXAMPLE 5

2-(5-Methylisoxazole-4-yl)methylthio-cycloheptoimidazole (Compound 34)

(a) 5-Methyl-4-chloromethylisoxazole

A mixture of 5-Methylisoxazole (23.7 g), paraformaldehyde (11.4 g) and zinc chloride (14.3 g) in 70 ml of dichloromethane was refluxed under the introduction of dry HCl gas. It was cooled, poured into water, and neutralized with sodium carbonate. The solution was extracted with chloroform and the solvent was evaporated in vacuo. 15.0 g of the desired compound was obtained M.S. (m/e) 132 (M⁺+1) b.p. 87° C. (18 mmHg).

(b) 2-(5-Methylisoxazole-4-yl)methylthio-cycloheptoimidazole (Compound 34)

Utilizing the same procedure as outlined in example 1, compound 34 was obtained from 5-methyl-4-chloromethylisoxazole [0.33 g, prepared by the above method (a)] and 2-mercapto-cycloheptoimidazole (0.4 g). m.p. 99°~100° C. M.S. (m/e) 256 (M⁺−1). I.R. 1635, 1428, 1450 cm⁻¹.

The following compounds were obtained by the same procedure as outlined in methods of example 5. They are shown in table 5.

EXAMPLE 6

2-(2-Pyridyl)methylthio-5-(1-methylamino)ethyl-cycloheptoimidazole (Compound 42)

0.14 g of 2-(2-Pyridyl)methylthio-5-acetylcycloheptoimidazole (Compound 23, prepared by the method of example 3) was dissolved in 40 ml of methanol, 2 ml of 40% methylamine-MeOH solution and 0.18 g of NaBH₄ were added to the methanol solution. The mixture was stirred for 2 hours at ambient temperature and concentrated to dryness in vacuo. The residue was extracted with chloroform and the chloroform was evaporated. Purification of the residue by chromatography [SiO₂, CHCl₃—MeOH (50:1)] gave an oily substance of the desired compound.

M.S. (m/e) 311 (m⁺+1), I.R. 2915, 2850, 1595, 1485, 1075 cm⁻¹.

TABLE 5

Structure: R-[cycloheptoimidazole]-S-(CH₂)ₙ-A

| Compound | R | n | A | m.p. (°C.) |
|----------|---|---|---|------------|
| 35 | H | 1 | 3,5-dimethylisoxazol-4-yl | 130~131° C. |
| 36 | H | 1 | 5-methylisoxazol-4-yl | 107° C. |
| 37 | H | 1 | 2-methyl-5-phenyloxazol-4-yl | 138~140° C. |
| 38 | H | 1 | 2-methyl-5-(4-methylphenyl)oxazol-4-yl | 110~112° C. |
| 39 | H | 1 | 2-methyl-5-(4-methoxyphenyl)oxazol-4-yl | 149~150° C. |
| 40 | H | 1 | 2-methyl-5-(4-chlorophenyl)oxazol-4-yl | 180~181° C. |

TABLE 5-continued

R-[cycloheptoimidazole]-S—(CH₂)$_n$—A

| Compound | R | n | A | m.p. (°C) |
|---|---|---|---|---|
| 41 | H | 1 | (5-methyl-3-phenylisoxazol-4-yl) | Oil |

EXAMPLE 7

2-(4-Nitrophenyl)methylthio-cycloheptoimidazole-S-oxide (Compound 43)

1.2 g of compound 23 was dissolved in 40 ml of chloroform and the solution was maintained at −30° C. and m-chloroperoxybenzoic acid (0.76 g in 10 ml of dichloroethane) was added dropwise. After stirring at −30° C. for 1 hour, the reaction mixture was raised to −10° C. Triethylamine (0.5 ml) of dilute NaHCO₃ solution were added; the solution was washed with water, dried (Na₂SO₄), and then concentrated to dryness in vacuo. The residue was washed with ethyl acetate and it gave 0.68 g of yellow crystals. Recrystallization of this compound with dilute alcohol gave 0.45 g of the desired compound. m.p. 179°∼180° C., M.S. (m/e) 313 (M+), I.R. 1512, 1413, 1347, 1302, 1062, 756 cm⁻¹.

The following compounds were obtained by the same procedure as outlined in method of example 7. They are shown in the table 6.

TABLE 6

R-[cycloheptoimidazole]-S(O)—(CH₂)$_n$—A

| Compound | R | n | A | m.p. (°C) |
|---|---|---|---|---|
| 44 | H | 1 | 2,3,4-trimethoxyphenyl | 147∼148° C. |
| 45 | H | 1 | 4-methylphenyl | 157∼158° C. |
| 46 | H | 1 | (3-phenyl-5-methylisoxazol-4-yl) | 98∼100° C. |
| 47 | H | 1 | 4-methoxyphenyl | 144∼145° C. |
| 48 | H | 1 | 2-pyridyl | 134∼138° C. |
| 49 | H | 1 | 4-(N,N-dimethylamino)phenyl | 158∼160° C. |
| 50 | H | 1 | 1H-pyrazol-3-yl | 161∼163° C. |
| 51 | H | 1 | 1H-imidazol-4-yl | 162∼164° C. |
| 52 | H | 1 | (5-methylisoxazol-3-yl) | 145∼147° C. |
| 53 | H | 1 | (3-methylisoxazol-5-yl) | 130∼131° C. |
| 54 | H | 1 | 2-aminophenyl | 120° C. |
| 55 | H | 1 | 2-(N,N-dimethylamino)phenyl | 90∼91° C. |
| 56 | H | 1 | 2-(N-methylamino)phenyl | 124° C. |

What is claimed is:

1. A compound of the formula:

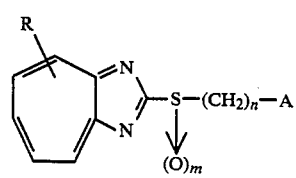

wherein:

R is a hydrogen atom, a lower-alkyl, acetyl, loweralkylaminoalkyl or 1-ethylenedioxyethyl group;

A represents a phenyl, pyridyl, benzimidazolyl, imidazolyl, thiazolyl, pyrazolyl, thiadiazolyl, oxazolyl or isoxazolyl group, each of which is optionally substituted by one or more members selected from the group consisting of an amino, methylamino, dimethylamino, nitro, methoxy, chloro, lower alkyl, methylaminomethyl, methylthio, piperidinomethyl, piperidinocarbonyl, methylenedioxy, diethoxymethyl, guanidino, and phenyl group, said phenyl group being optionally substituted by halogen, lower alkyl or alkoxy group;

m is 0 or 1, n is 1 or 2, or a pharmaceutically acceptable acid addition salt thereof.

2. The compound according to claim 1 in which A is a phenyl group which is optionally substituted by a lower alkyl, amino, methylamino, methylaminomethyl, nitro, methoxy, methylenedioxy, piperidinocarbonyl group or chlorine atom.

3. The compound according to claim 1 in which A is a pyridyl group which is optionally substituted by a diethoxymethyl, methylaminomethyl or piperidinomethyl group.

4. The compound according to claim 1 in which A is the imidazolyl, thiazolyl, pyrazolyl or thiadiazolyl group, said thiazolyl group being optionally substituted by an amino or guanidino group.

5. The compound according to claim 1 in which A is an oxazolyl or isoxazolyl group, each of which is optionally substituted by one or more members selected from the group consisting of the methyl, phenyl, tolyl, methoxyphenyl and chlorophenyl group.

6. The compound according to claim 1 in which A is a benzimidazolyl group which is optionally substituted by a methyl or amino group.

7. An anti-gastric ulcerative composition comprising a pharmaceutically acceptable carrier, and as an active ingredient, a compound defined in claim 1 in an amount effective to inhibit gastric ulcer.

* * * * *